United States Patent [19]

Audhya et al.

[11] Patent Number: 4,994,554

[45] Date of Patent: Feb. 19, 1991

[54] PROBURSIN

[75] Inventors: Tapan Audhya, Bridgewater; Gideon Goldstein, Short Hills; George Heavner, Flemington, all of N.J.

[73] Assignee: Immunobiology Research Institute, Inc., Annandale, N.J.

[21] Appl. No.: 287,462

[22] Filed: Dec. 20, 1988

Related U.S. Application Data

[63] Continuation-in-part of Ser. No. 192,482, May 11, 1988, abandoned.

[51] Int. Cl.$^5$ .................. A61K 37/24; C07K 5/08; C08F 283/00
[52] U.S. Cl. ............................ 530/327; 530/333; 530/334; 514/14; 525/54.1; 525/54.11; 436/86
[58] Field of Search ............... 530/327, 333, 334, 338; 514/14; 525/54.1, 54.11; 436/86; 935/11

[56] References Cited

U.S. PATENT DOCUMENTS 4,190,648  2/1980  Veber ................................. 514/11
4,291,022  9/1981  Sandrin et al. ..................... 514/11
4,584,284  4/1986  Audhya et al. ..................... 514/18

OTHER PUBLICATIONS

Brand, et al, Science, 193:319-321 (Jul. 23, 1976), [Brand I].
Brand, et al, Nature, 269:597-598 (Oct. 13, 1977) [Brand II].
Goldstein et al, Cold Spring Harbor Symposia on Quantitative Biology, XLI:5-8 (1977) [Goldstein I].
Goldstein, in "Molecular Control of Proliferation and Differentiation", pp. 197-202, Academic Press (1977) [Goldstein II].
Y. Stabinsky et al, Mol. Cell. Biochem., 30:71 (1980).
R. S. Hill et al, Diabetes, 34:115 (1985).
M. J. Berridge et al, Biochem. J., 212:473 (1983).

*Primary Examiner*—John Kight, III
*Assistant Examiner*—Nathan M. Nutter
*Attorney, Agent, or Firm*—Howson and Howson

[57] ABSTRACT

A multi-functional mammalian peptide probursin isolated in purified form, produced synthetically or recombinantly can be used therapeutically for treatment of immune disorders and tumor inhibition.

18 Claims, 5 Drawing Sheets

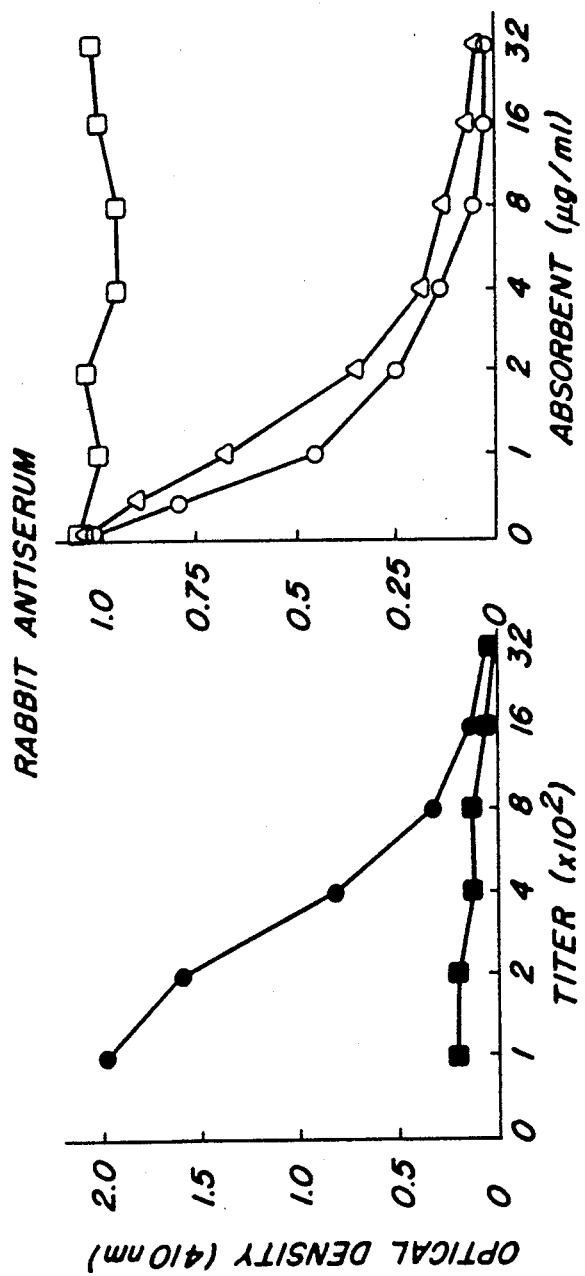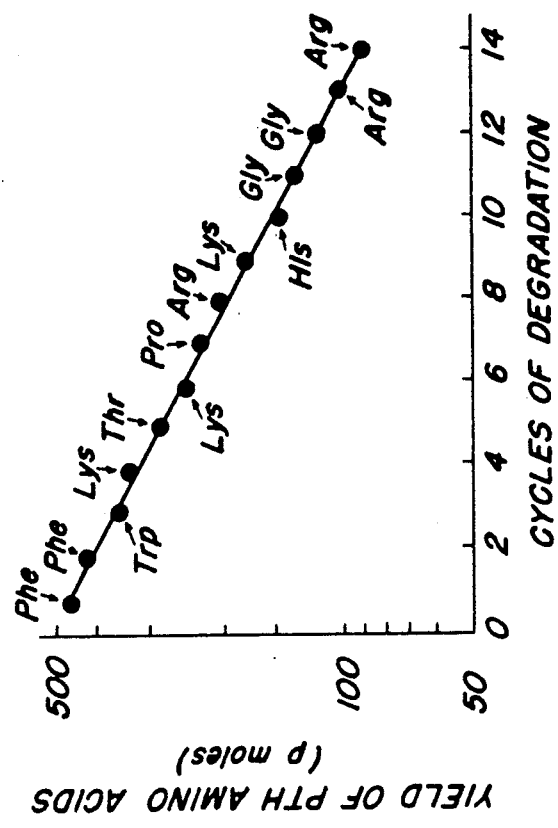

PROBURSIN

This is a continuation-in-part of pending U. S. patent application Ser. No. 07/192,482, filed May 11, 1988, now abandoned.

This invention relates generally to newly isolated proteins, and more particularly to proteins either isolated in purified form from mammalian intrahapatic bile ducts of the liver or from mammalian bone marrow. More particularly, the invention relates to a mammalian protein, probursin, which may be chemically synthesized or recombinantly reproduced. The invention also relates to therapeutic compositions containing probursin and methods for employing the same.

BACKGROUND OF THE INVENTION

The B lymphocytes, or B-cells, of the immune system of vertebrate animals provide an antibody response to a foreign antigen introduced into the body of the animal. In birds, precursor B-cells are differentiated in an organ called the bursa of Fabricius. In mammals, no equivalent organ to the bursa of Fabricius has been discovered and it has been considered that hematopoietic precursors to B-cells are present and may differentiate into mature B-cells within the bone marrow.

Until recently the hormonal inducer of the differentiation of B-cell precursors into B-cells has been unknown. However, in earlier studies by one of the present inventors and others, the existence of a specific B-cell differentiating inducer was demonstrated in the extracts of the bursa of Fabricius from chickens. This early work is reported in the following articles, which are incorporated herein by reference: Brand, et al, *Science*, 193:319-321 (July 23, 1976); Brand, et al, *Nature*, 269:597-598 (Oct. 13, 1977); Goldstein, et al, *Cold Spring Harbor Symposia on Quantitative Biology, XLI*:5-8 (1977); and Goldstein, in "Molecular Control of Proliferation and Differentiation", pgs. 197-202, *Academic Press* (1977).

More recently, the present inventors and others identified a tripeptide hormone called bursin, which has the amino acid sequence Lys-His-Gly-NH$_2$, as a specific inducer of B-cell differentiation. This peptide, also known as bursopoietin, is active in both birds and mammals and is described in U. S. Pat. No. 4,584,284 which is incorporated herein by reference.

Other endocrine peptides have been disclosed in the art. Somatostatin is a cyclic tetra-decapeptide produced by the hypothalamus and cells of the Islets of Langerhans. Somatostatin inhibits the release of a variety of hormones such as somatotropin, thyrotropin, corticotropin, insulin, glucagon, gastrin, secretin and renin. Another such regulating peptide is tuftsin, a basic tetra-peptide produced from circulating immunoglobulin, that stimulates phagocytosis in polymorphonuclear leucocytes and in macrophages. [See, e.g., V. A. Najjar et al, *Nature*, 228:672 (1970); A. Constantopoulos et al, *Cytobios.*, 6:97 (1972); and Y. Stabinsky et al, *Mol. Cell. Biochem.*, 30:71 (1980)].

The interrelationship of these hormones, including the B-cell differentiation factor bursin, has yet to be elucidated. The discovery of the association of a variety of hormones active in differentiating B-cells and providing effects on other tissues offers the potential for new treatments of immune disorders and liver dysfunction in humans and animals.

SUMMARY OF THE INVENTION

As one aspect of the present invention therefore, there is provided a 14 amino acid peptide obtained in purified form from mammalian bone marrow or liver. This peptide, probursin, may also be produced by standard synthetic chemical techniques. Alternatively, this peptide may be prepared by recombinant techniques.

Probursin has the ability, among others, to specifically induce differentiation of precursor bone marrow cells to B-cells. It is, therefore, highly useful in treating B-cell deficiencies of the immune system of humans and animals as well as in treating a variety of disorders of the liver. Additionally probursin functions to inhibit the release of growth hormone from the pituitary gland. The release of growth hormone correlates to the growth of certain cancerous tumors. Therefore, probursin is also useful in the treatment of certain cancers, specifically to effect tumor inhibition.

Another aspect of the invention is the provision of therapeutic compositions containing probursin. Still another aspect involves methods for use of these therapeutic compositions in the treatment of conditions or diseases involving insufficient B-cell differentiation due to deficiency or lack of B-cell differentiation factor, insufficient control of those hormones regulated by somatostatin and/or to enhance the ability of the immune system to phagocytose foreign particles in circulation. Other therapeutic methods using probursin involve treatment of cancers as referred to above.

Still further aspects of the invention are the provision of novel intermediates for synthetic or recombinant preparation of probursin, including novel peptide resin intermediates, novel vectors, and novel transformed host cells.

Other aspects and advantages of the present invention will become apparent based on the following detailed description of the presently preferred embodiments thereof.

BRIEF DESCRIPTION OF THE DRAWINGS

FIG. 3A is a graphical illustration of optical densities of various titers of anti-bursin antibody (dots) and rabbit serum (squares);

FIG. 3B is a graphical illustration of optical density vs. absorbant concentration of KLH-control conjugate (squares), KLH-bursin (triangles) and free probursin (circles);

FIG. 4 is a graphical depiction of yield of PTH amino acid per cycle of degradation;

DETAILED DESCRIPTION OF THE INVENTION

Figure 1:
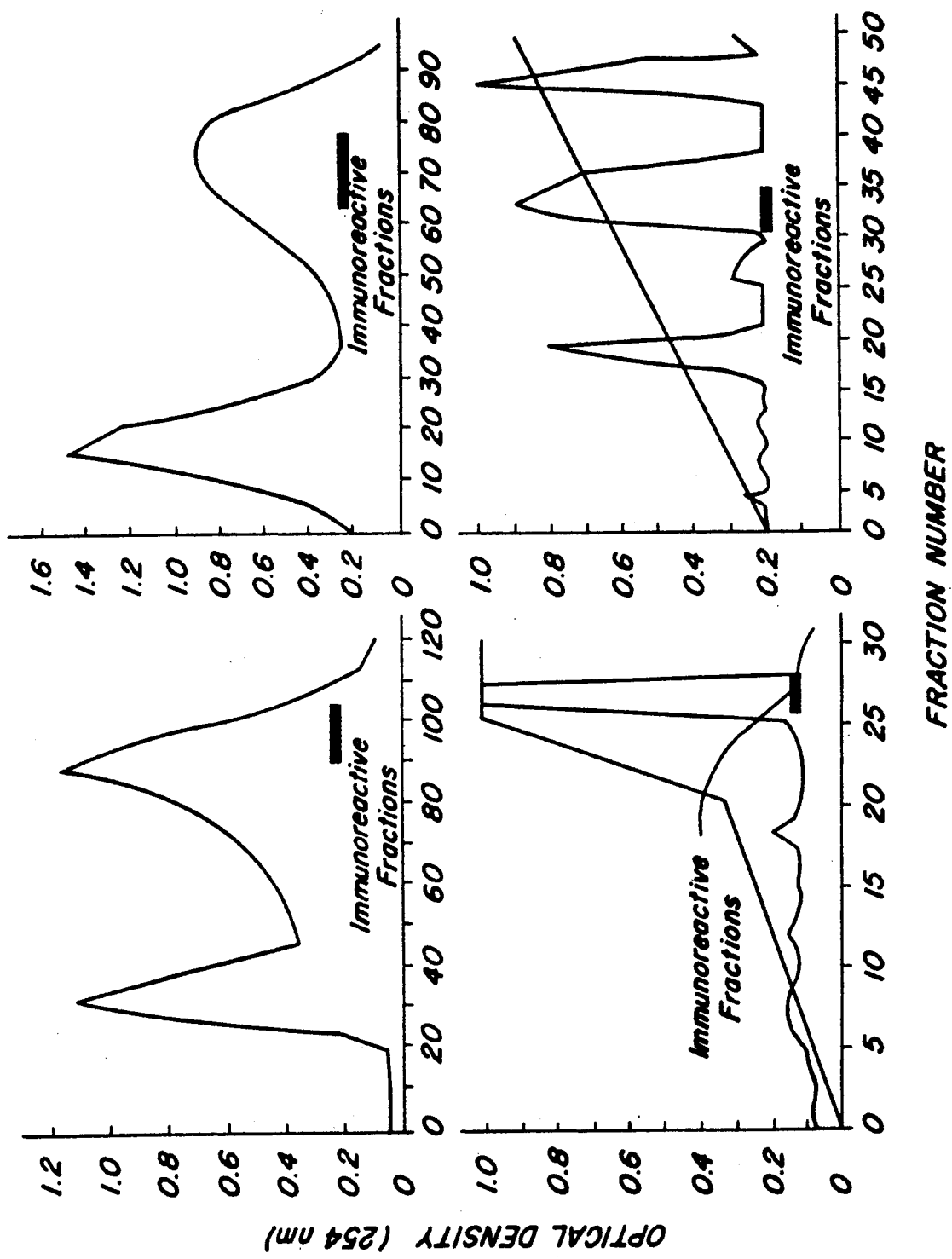
FIG. 1 is a graphical illustration of optical densities of purified fractions of probursin from bovine liver.

This invention provides a newly isolated mammalian polypeptide called probursin, which is characterized by the same or substantially the same sequence of amino acids:

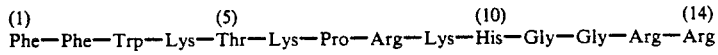

(1) (5) (10) (14)
Phe—Phe—Trp—Lys—Thr—Lys—Pro—Arg—Lys—His—Gly—Gly—Arg—Arg

The first five amino acid residues in the fourteen amino acid probursin sequence correspond to the active site of the hormone somatostatin. Amino acid residues 5 through 8 of probursin correspond to the active site of the human peptide tuftsin. Additionally, amino acid residues 9 through 11 of probursin correspond to the peptide bursin described above. These overlapping somatostatin, tuftsin and bursin sequences present in the probursin sequence are identical to the human sequences of the active sites of the peptides somatostatin, tuftsin and bursin. Thus, although the probursin polypeptide was initially isolated from fetal bovine liver, its sequence is believed to be substantially identical in other mammals, particularly humans.

In its broadest aspects, this invention provides mammalian probursin or an analog thereof in any form substantially free of native proteinaceous material, i.e. either isolated from mammalian liver or bone marrow, or synthesized or produced recombinantly. Variants of probursin including naturally occurring allelic changes in the sequence from mammalian species to species and among members of a single species, as well as deliberately introduced alterations in the sequence, such as by mutagenic or chemical techniques, or alterations occurring through use of various recombinant hosts, e.g., glycosylation changes, or by attachment of otherwise foreign molecules, e.g., radioactive labels and the like, are generically referred to throughout this specification as probursin analogs. Such analogs are encompassed by the present invention.

Preferably the mammalian probursin is human probursin. Probursin was initially isolated from bovine fetal liver by use of an antibody directed against bursin to monitor purification. The procedure for the isolation of probursin is described in Example 1 below. Mammalian probursin is isolated preferably from the liver; however, it may also be isolated from bone marrow by methods analogous to its isolation from bovine liver described in Example 1 below. While the polypeptide sequence of probursin is characterized by the same or substantially the same sequence as recited above, it is possible that allelic variants of the sequence, as well as variants of the sequence containing additional amino acids or native material may be obtained upon isolation from mammalian sources.

Additionally, the fourteen amino acid sequence of probursin may be chemically synthesized, providing a novel synthetic peptide. A presently preferred embodiment of the present invention is a synthetic peptide of the formula Phe-Phe-Trp-Lys-Thr-Lys-Pro-Arg-Lys-His-Gly-Gly-Arg-Arg and the pharmaceutically acceptable acid-addition salts thereof.

To prepare an acid addition salt of the polypeptide probursin the free polypeptide may be treated with an appropriate amount of acid. Acids capable of forming salts with the peptide of the invention include, but are not limited to, inorganic acids such as hydrochloric acid, hydrobromic acid, perchloric acid, nitric acid, thiocyanic acid, sulfuric acid, carbonic acid, phosphoric acid, and the like. Other acids useful for this purpose are organic acids such as formic acid, acetic acid, propionic acid, glycolic acid, lactic acid, pyruvic acid, oxalic acid, malonic acid, succinic acid, maleic acid, fumaric acid, anthranylic acid, cinnamic acid, naphthalenesulfonic acid, sulfonylic acid, and the like.

Synthetic production of the polypeptide of the invention may be according to the solid phase synthetic method described by Merrifield in *J.A.C.S.*, 85:2149–2154 (1963). This technique is well understood and is a common method for preparation of peptides. Alternative techniques for peptide synthesis are described in "Peptide Synthesis" by Bodanszky, et al, second edition, John Wiley and Sons, 1976. The solid phase method of synthesis involves the stepwise addition of protected amino acids to a growing peptide chain which is bound by covalent bonds to a solid resin particle. By this procedure, reagents and by-products are removed by. filtration, thus eliminating the necessity of purifying intermediates. The general concept of this method depends on attachment of the first amino acid of the chain to a solid polymer by a covalent bond. Succeeding protected amino acids are added, one at a time, or in blocks, in a stepwise manner until the desired sequence is assembled. Finally, the protected peptide is removed from the solid resin support and the protecting groups are cleaved off.

The invention also provides novel peptide-resin intermediates for preparation of the peptide of the invention. The intermediates have formulas the same or analogous to the following formula: $R^1$-Phe-Phe-($R^2$)Trp-($R^3$)Lys-($R^4$)Thr-($R^5$)Lys-Pro-($R^6$) Arg-($R^7$)Lys-($R^8$)His-Gly-Gly-($R^9$)Arg-($R^{10}$)Arg-Resin, wherein $R^1$ through $R^{10}$ represent suitable protecting groups on the appropriate locations of the indicated amino acids, and the resin is a suitable solid phase polymer which acts as a support for the reaction. Those of ordinary skill in the peptide synthesis art could select the appropriate amino protecting groups, hydroxyl protecting groups, indole-protecting groups, imidazole-protecting groups, and resin, disclosed, for example, in the references noted above. Those of skill in the art will also be able to construct similar peptide-resin intermediates for construction of modified peptides of this invention.

The amino acids may be attached to any suitable polymer. The resin must contain a functional group to which the first protected amino acid can be firmly linked by a covalent bond. Various polymers or copolymers are suitable for this purpose, such as cellulose, polyvinyl alcohol, polymethylmethacrylate, polystyrene, and polystyrene divinyl benzene. Appropriate protective groups usable in such synthesis and their abbreviations will be found in the above texts, as well as in J. F. W. McOmie, "Protective Groups in Organic Chemistry", Plenum Press, New York, 1973. Both of these books are incorporated herein by reference. The common protective groups used herein are t-butyloxycarbonyl (BOC), benzyl (BZL), t-amyloxycarbonyl (AOC), tosyl (TOS), o-bromo-phenylmethoxycarbonyl (BrZ), 2,6-dichlorobenzyl ($Cl_2$BZL), and phenylmethoxycarbonyl (Z or CBZ).

The general procedure of preparation of this peptide involves initially attaching the arginine (protected on its alpha amino and guanidino groups) to the resin. After attachment the resin is filtered, washed and the protecting group on the alpha amino group of arginine is removed. This protecting group is desirably t-butyloxycarbonyl. The removal of this protecting group must take place, of course, without breaking the bond between the arginine and the resin. To the resulting resin peptide is then coupled arginine protected on its alpha-amino and guanidino groups. This coupling takes place by the formation of an amide bond between the free carboxy group of the second arginine and the amino group of the first arginine attached to the resin. This sequence of events is repeated with successive amino acids until all amino acids are attached to the resin. Finally, the protected peptide is cleaved from the resin and the protecting groups removed to reveal the desired peptide. The cleavage techniques used to separate the peptide from the resin and to remove the protecting groups depend upon the selection of resin and protecting groups and are known to those familiar with the art of peptide synthesis.

The peptide may also be synthesized using standard solution peptide synthesis methodologies, involving either stepwise or block coupling of amino acids or peptide fragments using chemical or enzymatic methods of amide bond formation. These solution synthesis methods are well known in the art.

The polypeptide may also be produced by conventional recombinant technology. Conventional techniques for recombinant production of polypeptides may be found in Maniatis et al, in *Molecular Cloning, a Laboratory Manual*, Cold Spring Harbor Laboratory, Cold Spring Harbour, N.Y. (1982) and other references known and available to one of skill in the art. Thus, as part of this invention are all DNA sequences encoding probursin. These DNA sequences may differ by containing alternative codons encoding the same amino acid, modified or labelled bases, or the sequences may encode analogs of probursin. These sequences may form part of a DNA molecule containing suitable expression control sequences in operative association with the DNA sequences and capable of directing expression thereof upon transformation into host cells. These DNA molecules or vectors may be known vectors of bacterial yeast, fungal, insect or mammalian origin. The assembly of a probursin DNA sequence in association with known vector components is well within the ability of one of skill in the art. Similarly, the selection and transformation of microbial or mammalian host cells with the probursin-containing vectors of the invention are also conventional techniques available to those of skill in the art without employment of undue experimentation.

Both synthetic chemical and recombinant techniques for producing probursin may also be employed to modify the fourteen amino acid sequence of probursin as recited above. Such modifications may include deleting or replacing one or more of the fourteen amino acids in the above sequence or inserting or adding additional amino acids or chemical groups to the above sequence to enhance or direct the biological or pharmacological activities of the resulting peptide. For example, a variety of chemical groups may be attached to one or more of the amino acids of the peptide to provide a number of desirable characteristics, e.g. resistance to enzymatic degradation, enhanced half-life, and the like. Such modified forms of probursin are encompassed by the present invention.

Because probursin combines the overlapping active sites of three known regulatory peptides, probursin is believed to yield the same or analogous biological activities as possessed by somatostatin, tuftsin and bursin. Probursin is, therefore, therapeutically useful in the treatment of human and animals, since it has the capabilities of inducing the differentiation and maturation of B-cells which are involved in the immune responsiveness of the body. As a result of these characteristics the polypeptide has multiple therapeutic uses. This polypeptide has utility not only in research but in the treatment of humans and animals for diseases relating to a deficiency or absence of mature B-cells.

Probursin, fragments and analogs thereof are expected to demonstrate the capability of carrying out certain of the indicated functions of the liver (e.g. stimulating phagocytic activity of Kupffer cells and inhibiting pathological proliferation of hepatocytes). Thus, probursin, its fragments and analogs may have application in the treatment of various liver dysfunctions, such as cirrhosis.

Additionally, the subject peptides are considered useful in assisting the collective immunity of the body, in that they may be used to increase or assist in therapeutic stimulation of humoral immunity. The subject probursin polypeptides, analogs and therapeutic compositions containing same are generally considered to be useful in any area in which humoral immunity is an issue and particularly where there are deficiencies in immunity. Thus, where there is insufficient antibody production due to a deficiency of B-cells, the subject peptides can correct this condition by stimulating cell production. Probursin may therefore be useful in the treatment of patients with known immunodeficiencies, e.g., patients who fail to respond to vaccines, such as hemodialysis patients who do not develop antibodies to hepatitis vaccines and elderly patients who do not respond to pneumococcal vaccines.

For example, a typical condition which would be amenable to treatment with probursin is X-linked infantile hypogammaglobulinemia. This deficiency occurs almost exclusively in male children, and is believed to be due to the fact that children with this condition have precursor B-cells in their marrow and peripheral blood, which do not mature to antibody-secreting B-cells. Thus, patients having this condition suffer from chronic or recurring bacterial infection.

Other immunodeficiencies involving absent or lowered immunoglobulin production may also be amenable to treatment with the subject peptide, depending on the location of the immunological defect giving rise to this problem. If the defect is in the maturation of the pre-B-cell into the mature antibody-secreting B-cell, the subject peptide would be of use. It is well within the scope of the clinician of average skill in the art of treating immunodeficiencies to diagnose the point of defect for diseases amenable to treatment with probursin. See, e.g., "Basic and Clinical Immunology", Stites, Stobo, Fudenberg, and Wells, editors, 4th Ed. (1982) Lange Medical Publications, Los Altos, Calif. (Chapter 25).

Additionally, probursin has been found to inhibit the release of growth hormone (see Example 6). The inhibition of growth hormone has been correlated with the inhibition of certain cancerous tumor growth. [See, e.g., R. S. Hill et al, *Diabetes*, 34:115 (1985) and M. J. Berridge et al, *Biochem. J.*, 212:473 (1983)]. Thus probursin and/or its analogs or modified versions thereof has therapeutic use in the treatment of certain cancers in which tumor growth is inhibited by regulation of growth hormone.

Probursin and its analogs may also be employed as diagnostic agents, e.g., when associated with a radioactive or otherwise detectable label. Alternatively, probursin and its analogs may be employed on antigenic substances to develop polyclonal or monoclonal antibodies according to standard techniques, such as the Kohler-Milstein hybridoma methodologies.

The present invention therefore includes methods for regulating the immune system of a subject in need of such regulation which comprises administering to said subject an effective amount of one of the subject compounds.

The invention also provides a method for treatment of conditions resulting from relative or absolute deficiencies of liver functions of a subject which comprises administering to said subject a therapeutically-effective amount of probursin or an analog thereof.

The invention also provides a method for inducing the differentiation and maturation of B-cells which comprises administering to the subject a therapeutically effective inducing amount of probursin or an analog thereof.

The invention also provides a method for treating cancer by inhibiting tumor growth by administering to a patient a therapeutically effective growth hormone inhibiting amount of probursin or its analogs.

As used herein, the term "therapeutically-effective amount" means an amount which is effective to treat the respective conditions or deficiencies of the immune system or of the liver, as described above.

The invention further provides pharmaceutical compositions for practicing the above-identified methods of treatment. For use in pharmaceutical compositions, the peptide of the invention may be effective within the range of about 1 ug/kg to about 10 mg/kg. Probursin appears to be maximally active to about 100 ug/kg. One of ordinary skill in the immunodeficiency treatment art would readily be able to extrapolate from the results herein and select the appropriate dosage of the subject peptides for the appropriate clinical use without undue experimentation. For example, a treating physician would determine the dosage based on traditional clinical parameters including the age, weight, gender and overall physical condition of the patient.

This peptide is not limited by a specific mode of administration. However, the presently preferred mode of administration is parenteral, due to the potential of the sequence to be degraded by gastric enzymes. While the most desirable parenteral mode is sub-cutaneous, this peptide may also be administered percutaneously, intramuscularly, intrahasally, intraperitoneally, intravenously, buccally or via suppositories.

To prepare the pharmaceutical compositions of the present invention, the probursin may be combined as the active ingredient in intimate admixture with pharmaceutical carriers and/or excipients according to conventional pharmaceutical compounding techniques. This carrier may take a wide variety of forms depending on the form of preparation desired for administration, including agents in suspensions, elixirs, and solutions. For parenteral products, the carrier will usually comprise sterile water or saline solution. Other ingredients may be included to impart additional desirable features to the pharmaceutical product, e.g. to aid solubility or for preservation purposes. Injectable suspensions may also be prepared employing appropriate liquid carriers, suspending agents, and the like. Those of skill in the parenteral formulation art will readily recognize how to prepare such a composition.

The following examples illustrate the isolation of bovine probursin from fetal liver, a method for providing synthetic probursin, and assays demonstrating activities of the peptide. The invention is not limited by these examples.

EXAMPLE 1. Crude Extraction of Bursin and Probursin

Bovine fetal liver (500 g) was extracted with (25% w/v) ammonium bicarbonate buffer (50 mM, pH 8.0) containing 1 mM polymethylsulfonic acid (PMSF), 1 mM ethylene diamine triacetic acid (EDTA), and 1 mM betamercaptoethanol. The tissues were homogenized at 4° C. for 3 minutes in a blender and centrifuged (4° C.) for 45 minutes at 9000 rpm. The supernatants were filtered through a gauze. The cleaned filtrates were stored at -60° C. A 25 ml aliquot was lyophilized and suspended in 10 ml phosphate buffered saline (PBS).

The solution was centrifuged and 2.5 ml aliquots were subjected to PD-10 [Pharmacia] column chromatography. The low molecular weight retained fractions were lyophilized and were dissolved in 1 ml ammonium bicarbonate buffer (50 mM, pH 8.0) for the enzyme linked immunosorbant assay (ELISA) described in Example 2 below.

Probursin was further purified from bovine fetal liver by (A) gel filtration on a Sephadex G-75 molecular sieve column [Pharmacia] followed by (B) an ion exchange CM Sephadex column [Pharmacia]. Bursin, which contributed to the immunoreactivity of the fraction was removed during the performance of the next purification step (C) thin-layer chromatography. The resulting fraction (D) was again filtered on Sephadex G-75 and (E) the remaining filtrate was subjected to anion exchange fast protein liquid chromatography on a Mono-Q column [Pharmacia]. The final step of the purification was (F) reverse phase FPLC. The yields and order of the purification steps are illustrated in Table 1 below.

Figure 2:
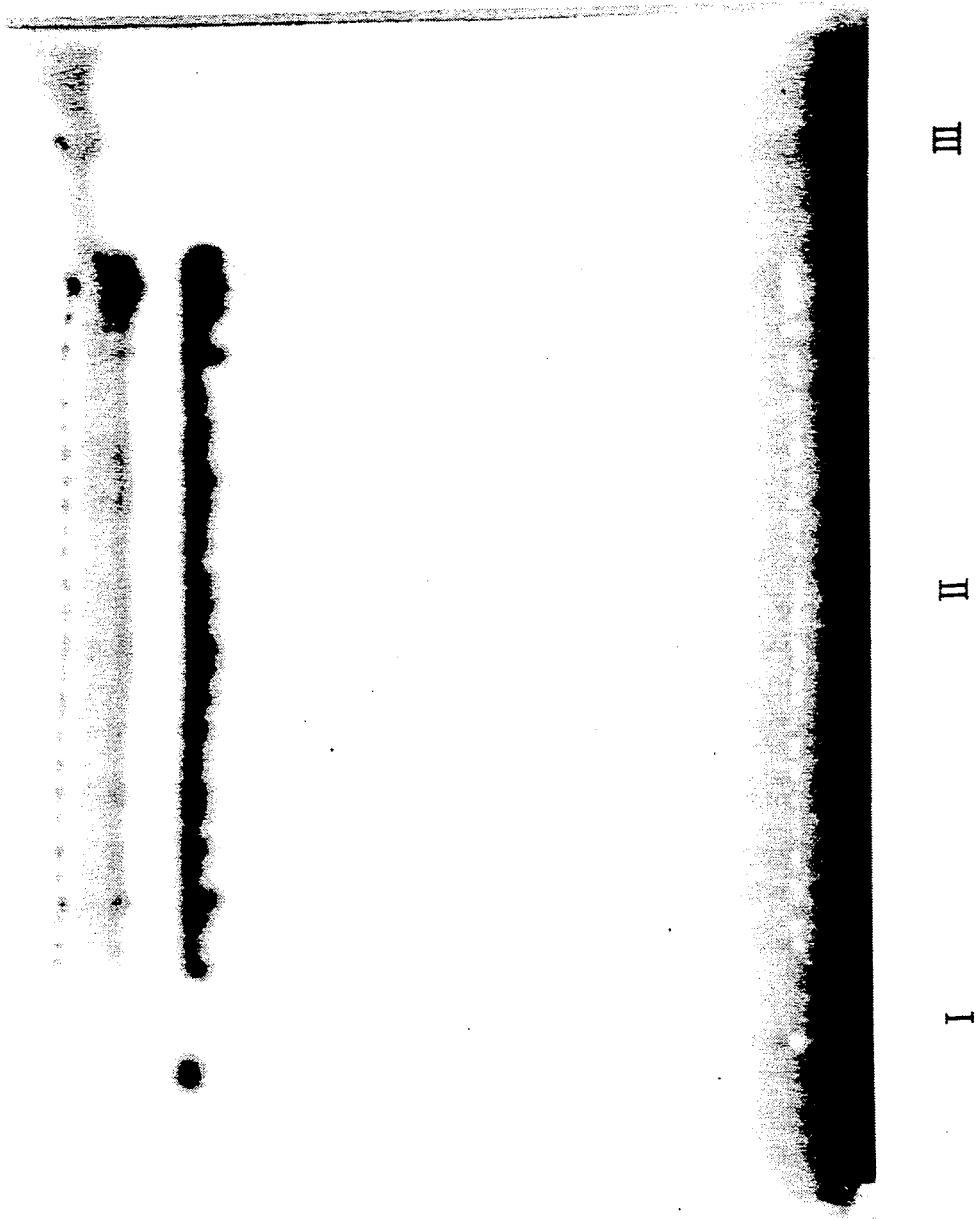
FIG. 2 is an illustration of a thin-layer chromatography gel of probursin.

Optical densities at 254 nm of the step-wise purified fractions was also evaluated. Graphs of the fractions of steps A, B, E and F are shown on FIG. 1. FIG. 2 illustrates a gel resulting from the thin-layer chromatography step C.

EXAMPLE 2. ELISA

A. Rabbit antiserum

For rabbit immunization, probursin was coupled to keyhole limpet hemocyanin (KLH) via 1-ethyl-3-(3-dimethylaminopropyl)-carbodiimide (ECDI) according to the method of Tamura et al, *Cell*, 34:587 (1983). Briefly, 5 mg of bursin was dissolved in 400 ul of water acidified by hydrochloric acid to pH 3.0, then cooled in an ice bath. Ten mg of ECDI in 20 ul volume was added and the resultant mixture was incubated for 15 minutes in an ice bath. Fifteen mg of KLH in 0.5 ml, pH 3.0, acidified water was added to this mixture. 0.5 ml of saturated ammonium carbonate solution was added to the solution and a small amount of dry ammonium carbonate was

TABLE I

PURIFICATION OF PROBURSIN FROM FETAL BOVINE LIVER

| Purification step | Total Probursin (mg) | Total Protein (mg) | Probursin (%) | Purification (fold) | Recovery (%) |
|---|---|---|---|---|---|
| Fetal liver (wet weight, 500 g) | — | 73400 | — | — | — |
| A Gel filtration, Sephadex G-75 | 92.6 | 7400 | 1.25 | 1 | 100 |
| B Ion exchange, CM Sephadex | 28.7 | 950 | 3 | 2 | 31 |
| C Thin-layer chromotography* | 6.4 | 91.2 | 7 | 5 | 7 |
| D Gel filtration, Sephadex G-25 | 2.6 | 27.4 | 10 | 8 | 2.8 |
| E Anion exchange FPLC, Mono-Q | 2.1 | 5.3 | 40 | 32 | 2.3 |
| F Reverse phase FPLC | 1.4 | 1.5 | 93 | 74 | 1.5 |

*Bursin, which contributed to immunoreactivity, was removed at this step.

added to keep the solution saturated. The mixture was incubated for three hours while stirring in an ice bath and then dialyzed against 2 liters of water each time with three changes over a 40-48 hour period and then PBS overnight. The conjugate was diluted with PBS to 1 mg/ml bursin.

Two hundred ug of KLH-bursin in 200 ul volume was mixed with 400 ul of complete Freund's adjuvant. Five hundred ul of this suspension was used to immunize each of the five rabbits subcutaneously at multiple sites. At 4-6 week intervals the rabbits were boosted with a similar suspension containing incomplete Freund's adjuvant.

B. ELISA protocol

Antisera were tested for activity in the following ELISA protocol. The assays were performed according to the method of Voller et al, *Bull. WHO*, 53:55 (1976). Briefly, polyvinyl chloride microtiter plates (Fisher Scientific, Springfield, N.J.) were coated overnight with 100 ul/well of 10 ug/ml solution of tetramer of probursin in 0.1 M phosphate buffer, pH 7.2. Plates were washed and were postcoated with 150 ul/well of 0.5 percent bovine serum albumin in PBS, pH 7.2, for one hour at room temperature. Plates were washed, dried at 37° C. for 6-24 hours and sealed in dessicated packages and stored at 4° C.

Antisera to be tested were diluted in PBS containing 0.05 percent Tween 20. One hundred ul of the diluted sera were added per well in triplicates. Normal rabbit or mouse serum was used as the negative control. After 60 minutes of incubation at room temperature the plates were washed three times with PBS Tween-20. One hundred ul of alkaline phosphatase conjugated to affinity-purified goat anti-rabbit IgG (heavy and light chains) diluted 1:2000 in PBS Tween-20 were added to each well. The plates were incubated at room temperature for 60 minutes. The plates were washed and 100 ul of 1 mg/ml of para-nitrophenyl-phosphate in diethanolamine buffer were added to each well. After 30 minutes of incubation at room temperature the reaction was terminated with the addition of 50 ul/well of 5 N NaOH and the optical density was read at 410 nm.

C. Results

Two of five rabbits developed antibodies to probursin after five months, the titers being approximately 1:800 (FIG. 3A). Anti-bursin antiserum binding was blocked by KLH-bursin and also by free probursin, but not by KLH-control conjugate (FIG. 3B).

EXAMPLE 3. Automated N-Terminal Protein Sequencing

Automated sequence analyses on intact probursin, and tryptic and cyanogen bromide fragments of probursin were performed by gas-phase sequencing that used a model 470A Applied Biosystems gas-phase sequencer with Polybrene as carrier and a standard single-coupling single-cleavage program. The resulting phenylthiohydantoin-derivatized amino acids were identified by HPLC with a 1084B Hewlett Packard highpressure liquid chromatograph. FIG. 4 illustrates the yields.

EXAMPLE 4. Preparation of a Synthetic Peptide of the Invention

The peptide was synthesized by the solid phase method on an ABI 430 Peptide Synthesizer using standard protocols for BOC-amino acid derivatives. The synthesis was begun with 0.50 mmols BOC-(Tos)Arg-PAM resin. The completed peptide resin weighed 1.87 g. The resin was treated with 20 ml HF and 2 g p-cresol at 0° C. for one hour. The HF was removed under reduced pressure and ethyl acetate was added to the residue. The mixture was filtered and washed with ethyl acetate. Trifluoroacetic acid was added to the solids and the mixture filtered. The filtrate was evaporated to small volume, then ether added. The precipitate was filtered and washed well with ether yielding 1.04 grams of a white solid. A 440 mg portion of this product was added to 50 ml of 1 M ammonium bicarbonate pH 9.0 to deformylate the Trp. The solution was deoxygenated with nitrogen purging and allowed to stand for 16 hours in a sealed flask. The solution was then diluted with water and lyophilized.

The peptide was purified by preparative HPLC on a Partisil-ODS M-20 column eluted with 20% acetonitrile/0.1% TFA. The peptide was dissolved with addition of dilute TFA to about pH 3 and injected in 5 portions. The center fractions of the major peak were combined, organic solvent removed by rotary evaporation and the residue lyophilized. The product was converted to the acetate salt by passage through a column of Amberlite IR-68 anion exchange resin. The lyophilized product having the sequence below weighed 102 mg. phenylalanyl-phenylalanyl-tryptophyl-lysyl-threonyl-lysyl-prolyl-arginyl-lysyl-histidyl-glycyl-glycyl-arginyl-arginine.

| TLC (silica gel 60): | | |
|---|---|---|
| $R_f$ 0.10 | n-BuOH:HOAc:H$_2$O:pyr | 4:2:3:1 |
| $R_f$ 0.04 | EtOAc:pyr:HOAc:H$_2$O | 5:5:1:3 |

EXAMPLE 5. Biological Activity—Cyclic GMP Assay

Daudi cells were freshly seeded and grown for 2 days with harvesting as described in T. Audhya et al, *Arch. Biochem Biophys.*, 234:167–177 (1984). The cells were washed 3 times in PBS and resuspended in RPMI 1640 at a concentration of $1.0 \times 10^7$ cells/ml and were allowed to equilibrate at 37° C. for 30 minutes before the addition of the test compounds (25 ul) of bursin and probursin, and control peptides porcine insulin (A), equine myoglobin (B) and bovine growth hormone (C). The incubation was allowed to proceed in a shaking water bath for 4–5 minutes and was then terminated by addition of 1 ml ice-cold TCA (10%).

The cells in TCA were homogenized and sonicated to release cyclic nucleotide. The suspension was centrifuged at 3000×g for 20 minutes at 4° C. The resulting precipitate was dissolved in 0.1 N NaOH to determine the protein content. TCA was removed from the supernatant fraction by extracting 4 times with 5 ml of water-saturated diethyl ether. After the final extraction, the remaining traces of ether were removed by heating for 10 minutes in a 50° C. water bath. After lyophilization the sample was reconstituted in 50 MM acetate buffer (pH 6.2) for radioimmunoassay of cyclic GMP.

Figure 5A:
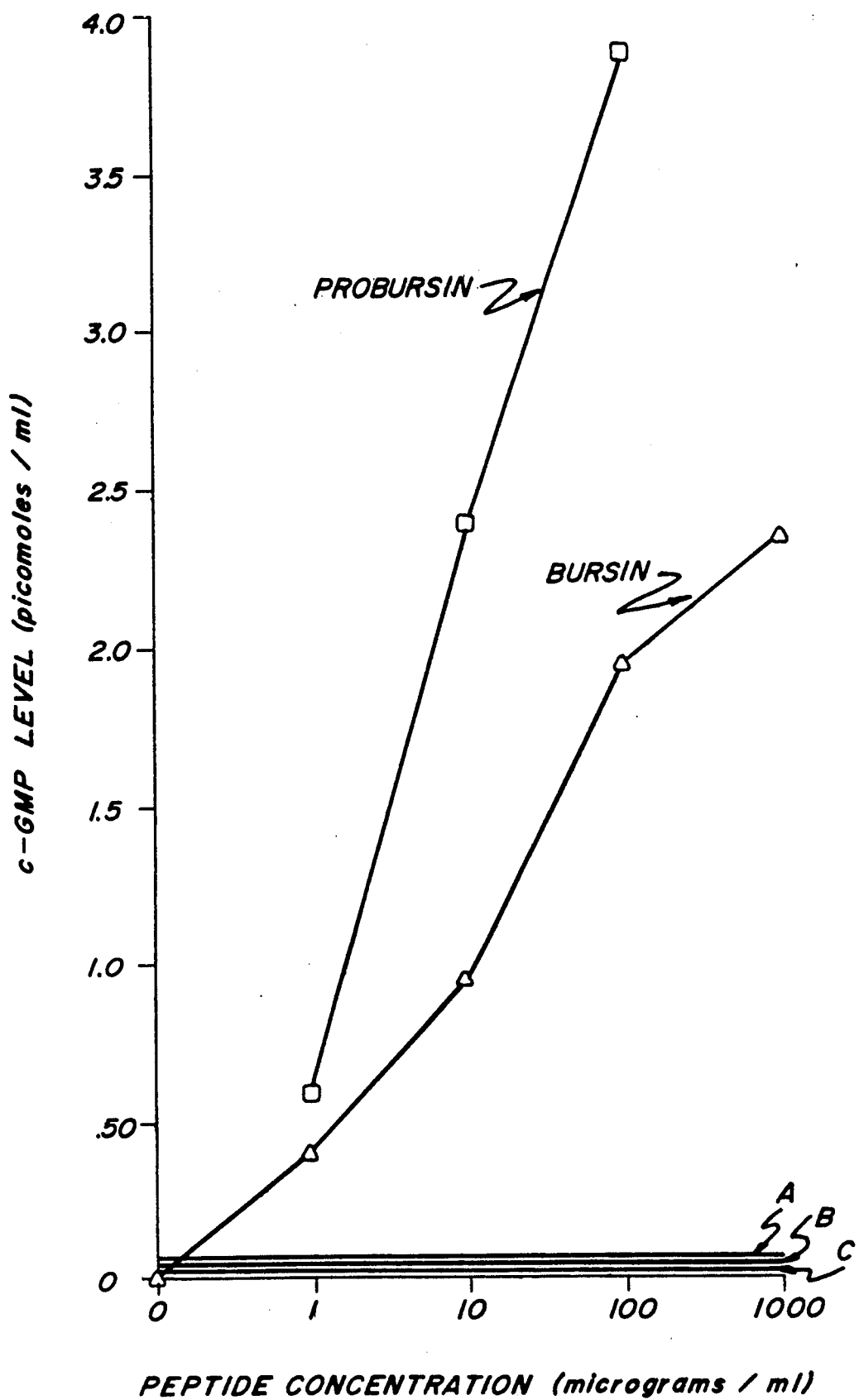
FIG. 5A is a graphical illustration of intracellular cyclic GMP levels in Daudi cells after incubation with probursin, bursin, porcine insulin (A), equine myoglobin (B) and bovine growth hormone (C)
Figure 5B:
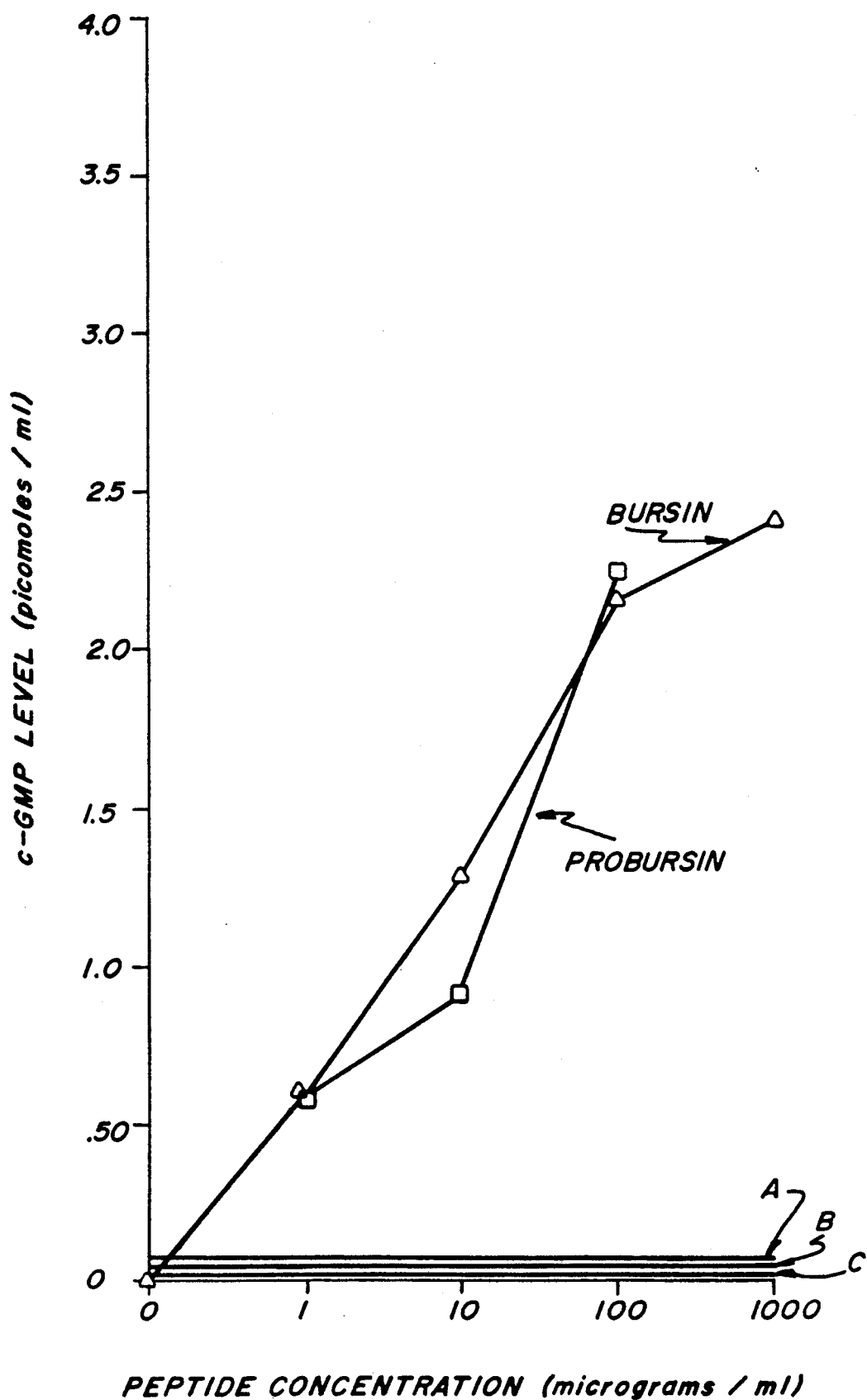
FIG. 5B is a graphical illustration of intracellular cyclic GMP levels in MOPC-315 cells after incubation with probursin, bursin and A, B and C, identified above, as controls.

Dose-response curves from 0 to 1000 micrograms/ml were evaluated for bursin, probursin and controls. FIG. 5 shows typical dose-response curves for active bursin and probursin and inactive compounds in Daudi cells (FIG. 5A) and in MOPC-315 cells (FIG. 5B). A threshold activity was determined for each peptide tested. This is defined as the lowest concentration of the test peptide (1 ug/ml) which induced an intracellular level of cyclic GMP greater than two standard deviations above the control. The controls had intracellular cyclic GMP values of less than 0.1 picomoles/ml (mean±standard deviation). Test results were considered positive if the level of cyclic GMP was greater than 1.52 times (2 standard deviations) that determined for the parallel negative control.

EXAMPLE 6. Biological Activity—Growth Hormone Inhibition

An assay was performed to study the effect of probursin in combination with growth hormone releasing factor (GRF) as this combination effects the release of $^3$H inositol phosphate (IP) and growth hormone (GH) accummulation in SV40 transformed hamster beta cells (HIT). The experiment was performed according to the procedures described in M. J. Berridge et al, cited above.

Briefly described, commercially available HIT cells were incubated at 37° C. for 1 hour in metabolic RPMI medium with 5% fetal calf serum (FCS). GRF in varying concentrations indicated in the Table below was added to the cell culture and incubated for 15 minutes at 37° C. The cells were then centrifuged at 800 rpm and the supernatant collected. Levels of GH and IP were measured in the supernatant by radioimmunoassay (RIA) also according to Berridge et al. These measurements formed the GRF control.

The same procedure was followed without the addition of GRF and is indicated below as the control.

Similarly, to indicate the effect of probursin on GRF, the procedure above was followed except that GRF and probursin at the appropriate concentrations indicated in the Table below were added to the cells together and followed by 15 minutes incubation and centrifugation. When the supernatant was measured by RIA as described above, the resulting concentrations of IP and GH were determined as illustrated in the Table below.

The data indicated in the Table below illustrates that probursin displays marked suppression of the effect of growth hormone releasing factor, similar to that of somatostatin as described in Hill et al, cited above.

Table

|  | [IP] (cpm) | [GH] (n/ml) |
| --- | --- | --- |
| Control | 15 ± 4 | 14 ± 2 |
| GRF (0.1 nM) | 489 ± 19 | 162 ± 4 |
| GRF (0.1 nM) + Probursin (.1 μM) | 239 ± 13 | 35 ± 4 |
| GRF (1 nM) | 2810 ± 290 | 648 ± 26 |
| GRF (1 nM) + Probursin (0.1 μM) | 1911 ± 310 | 480 ± 31 |
| GRF (1 nM) + Probursin (1.0 μM) | 444 ± 22 | 77 ± 6 |
| GRF (10 nM) | 8962 ± 821 | 1162 ± 84 |
| GRF (10 nM) + Probursin (10.0 μM) | 382 ± 16 | 29 ± 3 |

The invention has been described herein with reference to certain preferred embodiments, however, numerous variation and modification of the invention will occur to those of skill in the art which modifications are believed to be encompassed by the appended claims.

We claim:

1. A peptide comprising the same or substantially the same amino acid sequence of formula Phe-Phe-Trp-Lys-Thr-Lys-Pro-Arg-Lys-His-Gly-Gly-Arg-Arg, analogs thereof, and the pharmaceutically acceptable acid-addition salts thereof.

2. The peptide according to claim 1 prepared by chemical synthesis.

3. The peptide according to claim 1 purified from mammalian cells.

4. The peptide according to claim 3 wherein said mammalian cells are human hepatic cells or cells of human bone marrow.

5. The peptide according to claim 1 prepared by recombinant techniques.

6. The peptide according to claim 1 substantially free from other mammalian proteinaceous materials.

7. The peptide according to claim 1 characterized by a threshold activity in inducing intracellular cGMP elevations in Daudi or MOPC-315 cells at concentrations of about 1 ug/ml, 8. A peptide having the sequence Phe-Phe-Trp-Lys-Thr-Lys-Pro-Arg-Lys-His-Gly-Gly-Arg-Arg, and pharmaceutically acceptable acid-addition salts thereof.

9. A therapeutic composition for treatment of immune disorders comprising an effective amount of the peptide of claim 1 in a pharmaceutically acceptable formulation.

10. The composition of claim 9 wherein said effective amount comprises between about 1 μg to about 10 mg/kg said peptide/kg of patient body weight.

11. A therapeutic composition for treatment of cancerous tumors comprising the peptide of claim 1 in or pharmaceutically acceptable formulation in an amount effective to inhibit the release of growth hormone in amounts sufficient to thereby inhibit growth of said tumor.

12. The composition of claim 11 wherein said effective amount comprises between about 1 μg to about 10 mg/kg said peptide/kg of patient body weight.

13. A method for regulating the immune system of a patient comprising administering to said patient an effective amount of the peptide of claim 1.

14. The method according to claim 13 wherein said peptide is administered parenterally.

15. A method for treating a patient having a deficiency in liver function comprising administering to said patient an effective amount of the peptide of claim 1.

16. A method for inhibiting the growth of a tumor in a patient comprising administering to said patient an effective amount of the peptide of claim 1.

17. A peptide-resin intermediate of formula: $R^1$-Phe-Phe-($R^2$)Trp-($R^3$)Lys-($R^4$)Thr-($R^5$)Lys-Pro-($R^6$) Arg-($R^7$)Lys-($R^8$)His-Gly-Gly-($R^9$)Arg-($R^{10}$)Arg-resin wherein $R^1$ through $R^{10}$ are each independently selected from appropriate protecting groups, and resin is an appropriate solid phase polymer.

18. A diagnostic reagent comprising the peptide of claim 1 or an antibody to said peptide.

* * * * *

UNITED STATES PATENT AND TRADEMARK OFFICE
CERTIFICATE OF CORRECTION

PATENT NO. : 4,994,554

DATED : February 19, 1991

INVENTOR(S) : Tapan Audhya, Gideon Goldstein, and George Heavner

It is certified that error appears in the above-identified patent and that said Letters Patent is hereby corrected as shown below:

Col. 7, line 53, delete "intrahasally" and insert -- intranasally --.

Col. 10, line 60, above Example 5, insert

-- Amino acid analysis:

Thy - 0.88, Pro - 1.04, Gly - 2.01, Phe - 2.00, His - 1.02, Lys - 2.91, Trp - 0.81, Arg - 3.14; 73% peptide. --

Col. 12, line 5, last column heading in table, delete "[GH] (n/ml)" and insert -- [GH] (ng/ml) --.

UNITED STATES PATENT AND TRADEMARK OFFICE
CERTIFICATE OF CORRECTION

PATENT NO. : 4,994,554

DATED : February 19, 1991

INVENTOR(S) : Tapan Audhya, Gideon Goldstein, and George Heavner

It is certified that error appears in the above-identified patent and that said Letters Patent is hereby corrected as shown below:

Col. 12, Claim 1, insert claim language (underlined) which was omitted by the Patent Office (see Claim 1 below):

1. A peptide comprising the same or substantially the same amino acid sequence of formula Phe-Phe-Trp-Lys-Thr-Lys-Pro-Arg-Lys-His-Gly-Gly-Arg-Arg, <u>naturally-occurring allelic variants thereof,</u> analogs of <u>said peptide characterized by the same biological activities</u> thereof, and the <u>pharmaceutically acceptable acid-addition salts thereof.</u>

Col. 14, Claim 18, delete "or an antibody to said peptide".

Signed and Sealed this

Twelfth Day of January, 1993

Attest:

DOUGLAS B. COMER

Attesting Officer     Acting Commissioner of Patents and Trademarks